United States Patent
Zimmer et al.

(10) Patent No.: US 7,141,520 B2
(45) Date of Patent: Nov. 28, 2006

(54) ANTIMICROBIAL ALKALI-SILICATE GLASS CERAMIC AND THE USE THEREOF

(75) Inventors: José Zimmer, Ingelheim (DE); Jörg Hinrich Fechner, Mainz (DE)

(73) Assignee: Schott AG, Mainz (DE)

( * ) Notice: Subject to any disclaimer, the term of this patent is extended or adjusted under 35 U.S.C. 154(b) by 0 days.

(21) Appl. No.: 10/498,244

(22) PCT Filed: Dec. 11, 2002

(86) PCT No.: PCT/EP02/14044

§ 371 (c)(1),
(2), (4) Date: Jun. 24, 2004

(87) PCT Pub. No.: WO03/050051

PCT Pub. Date: Jun. 19, 2003

(65) Prior Publication Data

US 2005/0009682 A1    Jan. 13, 2005

(30) Foreign Application Priority Data

Dec. 12, 2001  (DE) .................. 101 61 074
Sep. 7, 2002   (DE) .................. 102 41 495

(51) Int. Cl.
*C03C 10/04*   (2006.01)
*A01N 59/00*   (2006.01)

(52) U.S. Cl. .................. 501/5; 424/59; 424/602; 424/722; 424/744

(58) Field of Classification Search .................. 501/5, 501/10, 33; 65/33.1; 424/59, 405, 602, 424/682, 688, 722, 724
See application file for complete search history.

(56) References Cited

U.S. PATENT DOCUMENTS

| | | | |
|---|---|---|---|
| 5,676,720 A | 10/1997 | Ducheyne et al. | 65/17.5 |
| 5,681,872 A | 10/1997 | Erbe | 523/114 |
| 5,981,412 A | 11/1999 | Hench et al. | 501/5 |
| 2003/0167967 A1* | 9/2003 | Narhi et al. | 106/35 |
| 2004/0065228 A1* | 4/2004 | Kessler et al. | 106/35 |
| 2004/0167006 A1* | 8/2004 | Apel et al. | 501/10 |
| 2005/0009682 A1* | 1/2005 | Zimmer et al. | 501/5 |
| 2005/0031703 A1* | 2/2005 | Beier et al. | 424/601 |
| 2005/0069592 A1* | 3/2005 | Fechner et al. | 424/604 |
| 2005/0142077 A1* | 6/2005 | Zimmer et al. | 424/57 |

FOREIGN PATENT DOCUMENTS

| | | | |
|---|---|---|---|
| DE | 10241495 | * | 9/2003 |
| KR | 9200150 | | 1/1992 |
| WO | WO 01/03650 | | 1/2001 |
| WO | WO 01/04252 | | 1/2001 |
| WO | WO03/050051 | * | 6/2003 |
| WO | WO03/050053 | * | 6/2003 |

* cited by examiner

*Primary Examiner*—Karl Group
(74) *Attorney, Agent, or Firm*—Baker & Daniels

(57) ABSTRACT

The invention relates to a glass ceramic, wherein the initial glass comprises 30–65 percent (by weight) $SiO_2$; 5–30 percent (by weight) $Na_2O$; 5–30 percent (by weight) CaO, and 0-15 percent (by weight) $P_2O_5$, and wherein the main crystalline phases comprise alkali—alkaline earth—silicate and/or alkali silicate and/or alkaline earth silicate. The invention is characterized in that either a glass ceramic with a single crystalline phase 1 $Na_2O$—$2CaO$—3 $SiO_2$ is excluded, or the crystalline size of the glass ceramic is <10 μm, or the weight fraction of $SiO_2$ is <47%.

13 Claims, 19 Drawing Sheets

RIBBONS

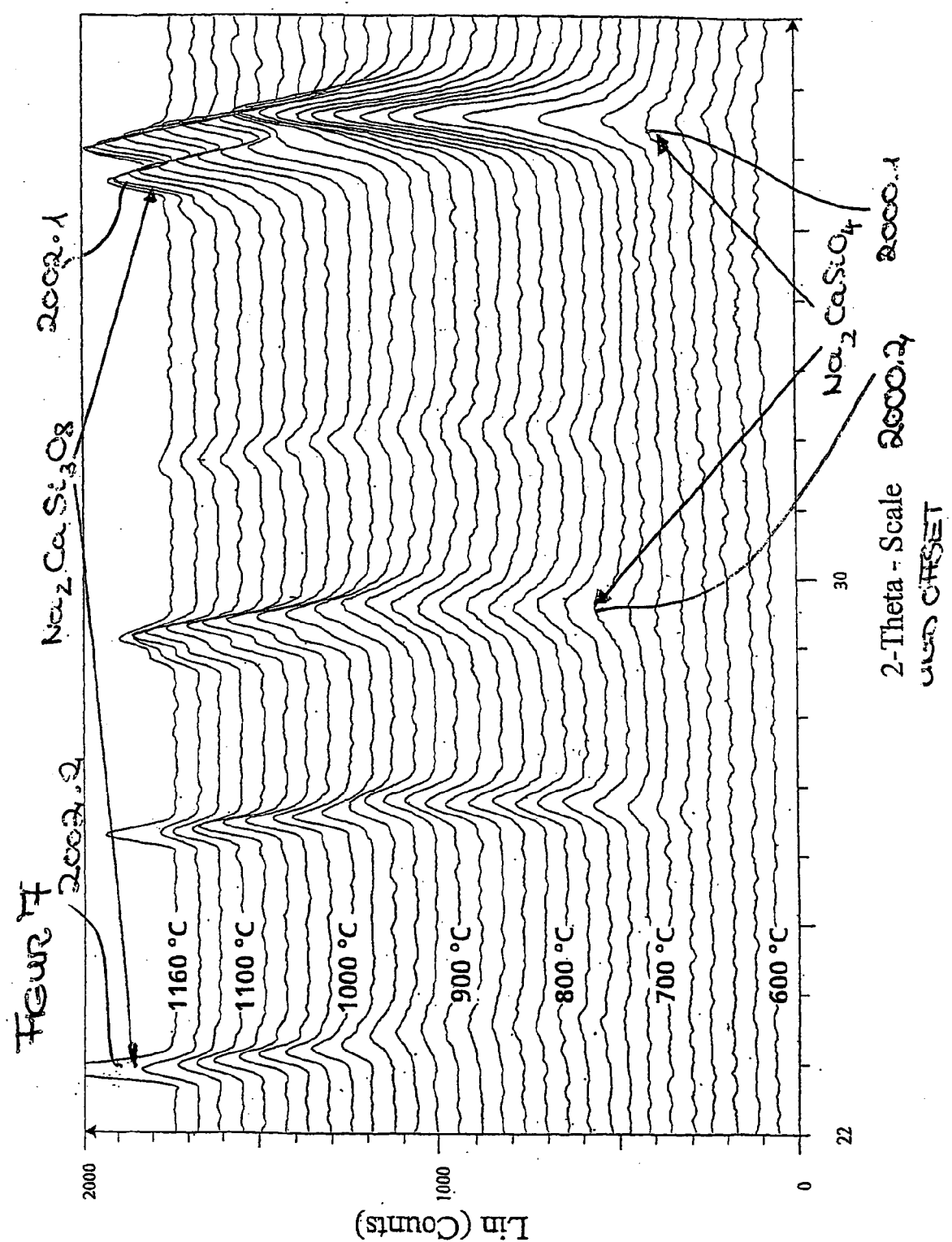

FIG. 8: An X-ray diffraction diagram of a glass ceramic powder from an initial glass according to the design example 8, ceramized at a temperature of 650°C for 4 hours
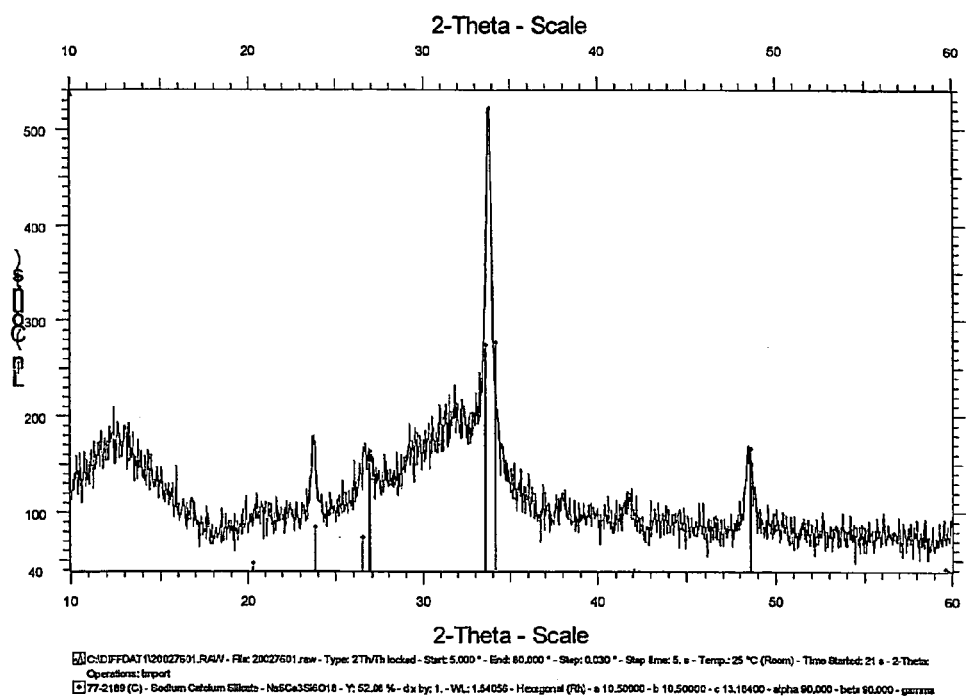

FIG. 9: An X-ray diffraction diagram of a glass ceramic powder from an initial glass according to the design example 8, ceramized at a temperature of 700°C for 4 hours
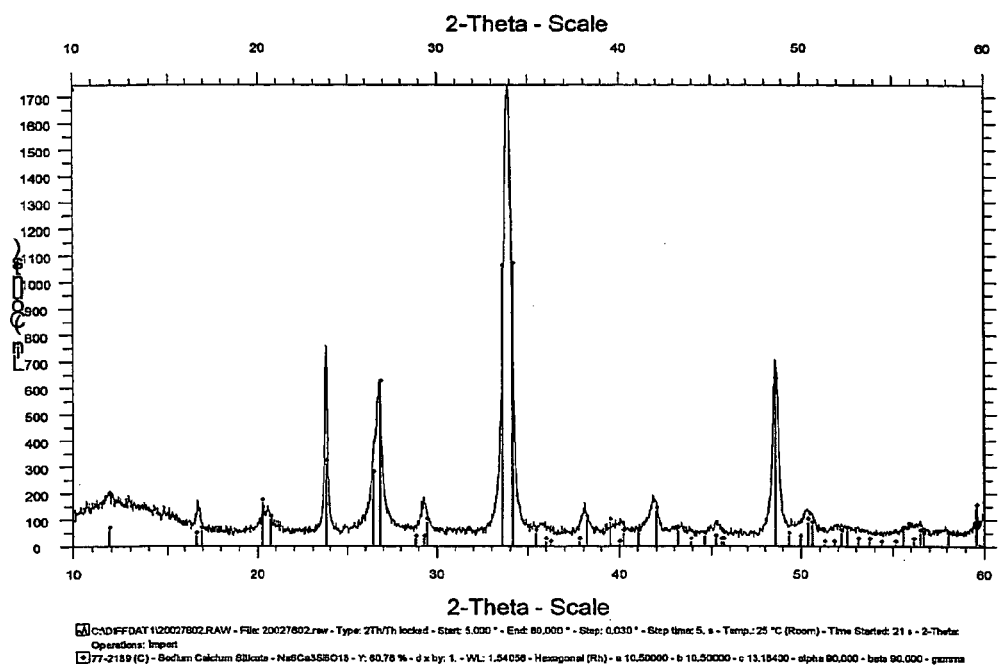

FIG. 10: An X-ray diffraction diagram of a glass ceramic powder from an initial glass according to the design example 8, ceramized at a temperature of 900°C for 4 hours
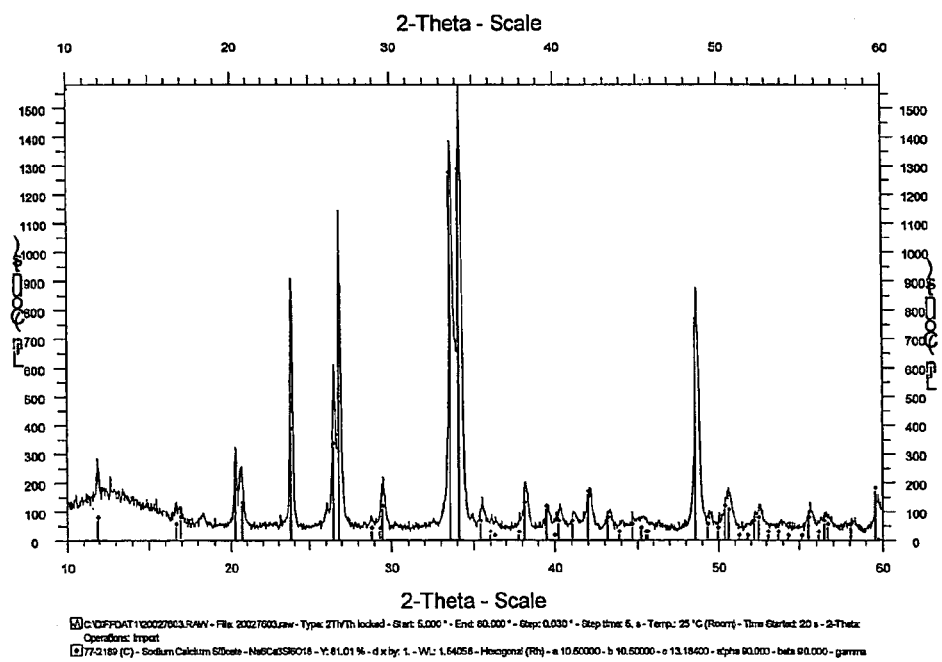

FIG. 11: An X-ray diffraction diagram of a glass ceramic powder from an initial glass according to the design example 9, ceramized at a temperature of 560°C for 4 hours
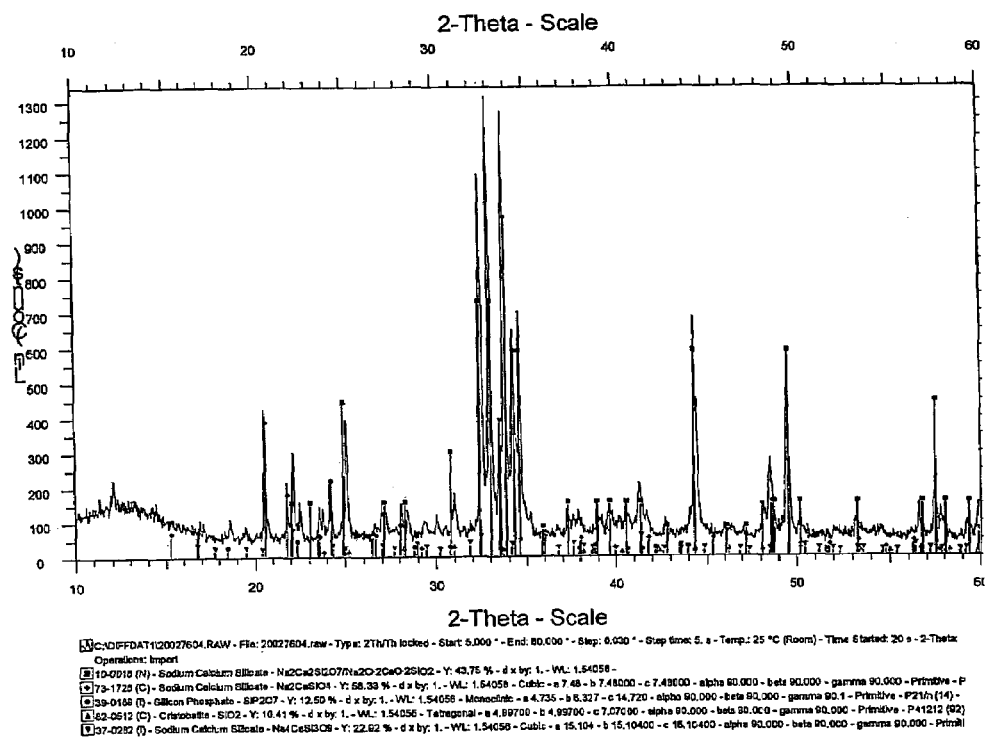

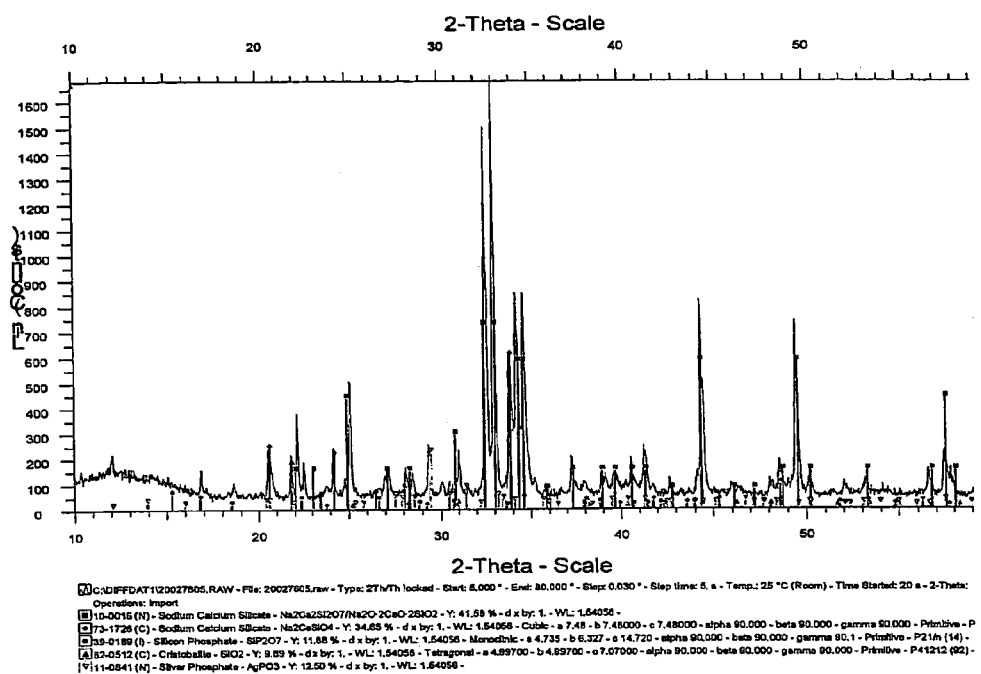
FIG. 12: An X-ray diffraction diagram of a glass ceramic powder from an initial glass according to the design example 9, ceramized at a temperature of 700°C for 4 hours

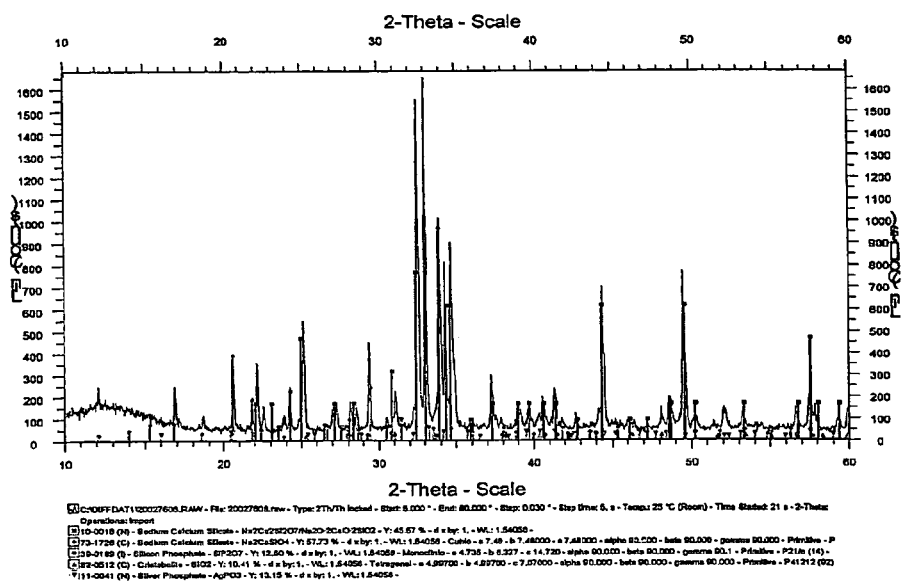
FIG. 13: An X-ray diffraction diagram of a glass ceramic powder from an initial glass according to the design example 9, ceramized at a temperature of 900°C for 4 hours

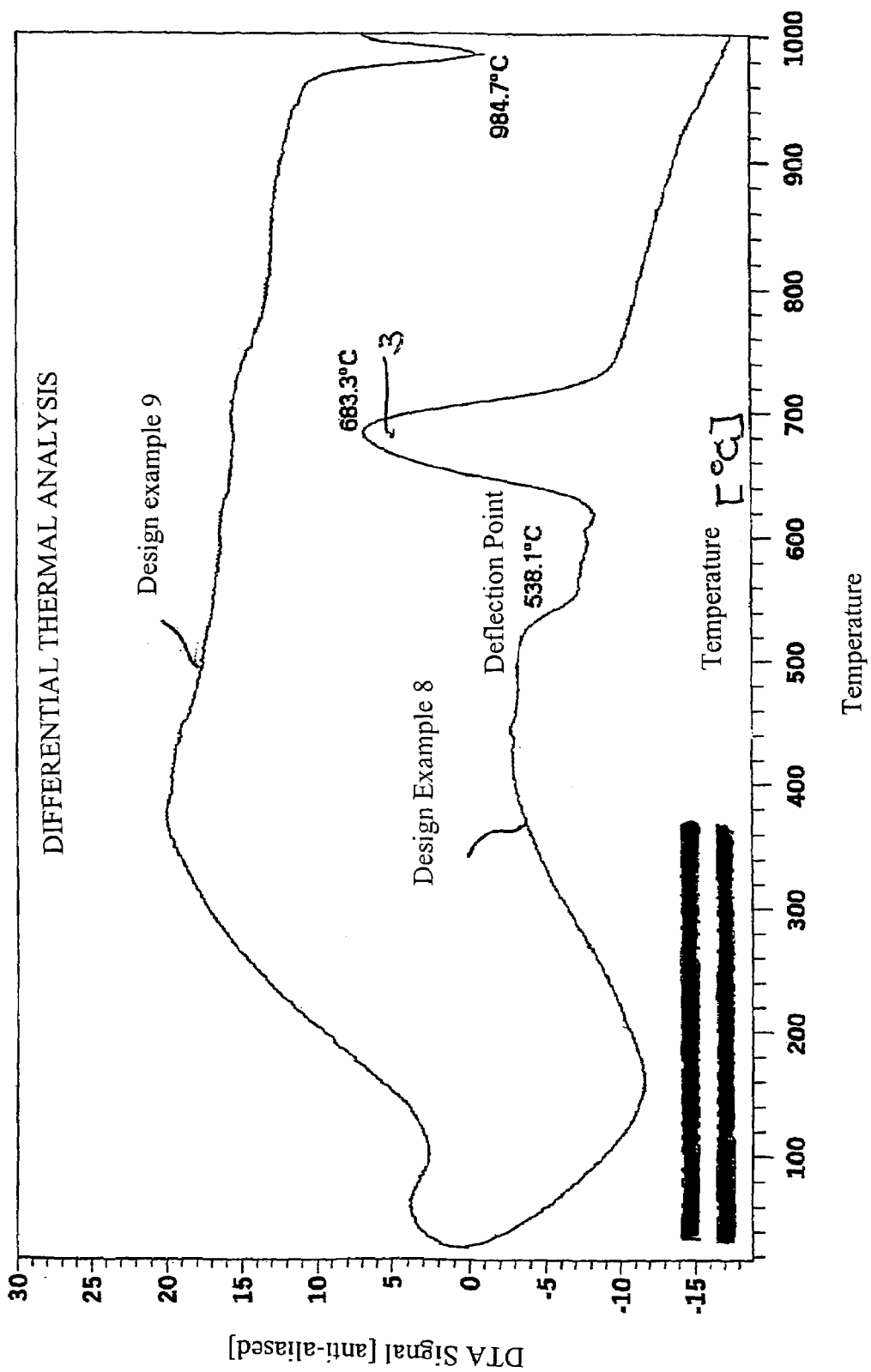

FIG. 15: Standardized conductivity of glass ceramics from a initial glass with a according to the design example 1 ceramized at various temperatures (standardized for the surface)
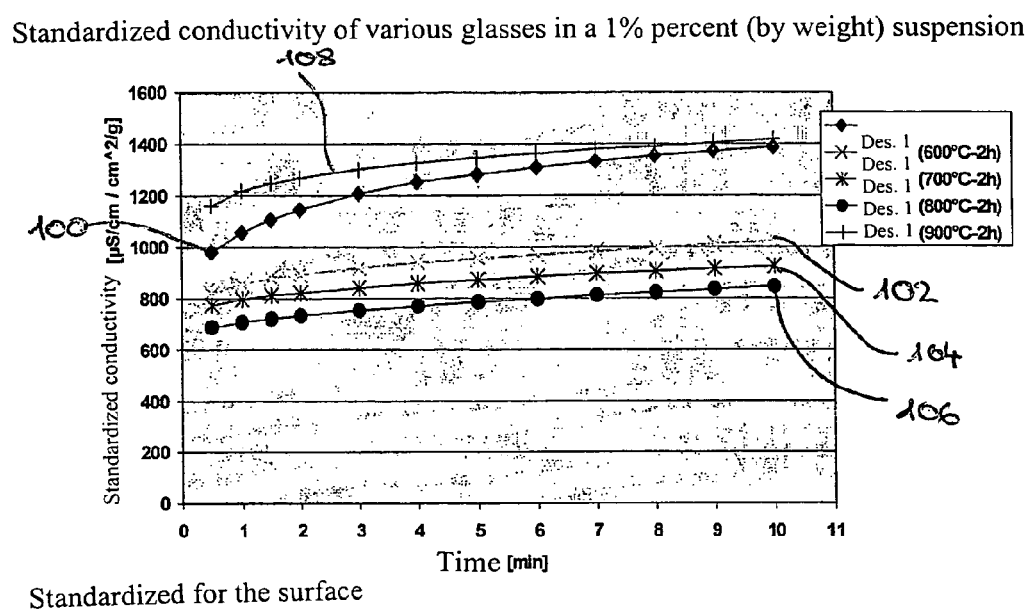
Standardized for the surface FIG 16: Standardized bacidity of glass ceramics from a initial glass with a according to the design example 1 ceramized at various temperatures (standardized for the surface)
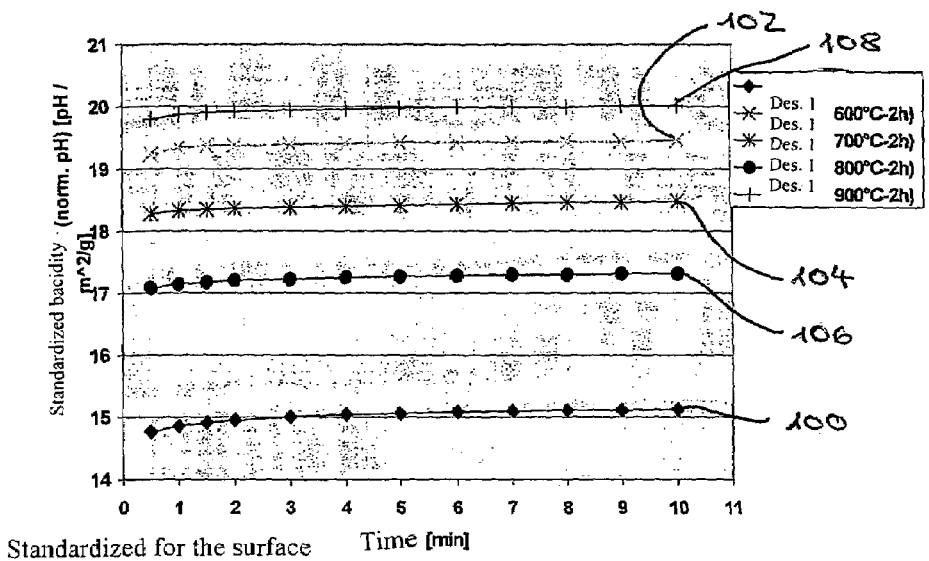

FIG 17:    An SEM image of surface crystals on the surface of a glass ceramic that has been obtained by annealing at a temperature of 660°C for 4 hours.
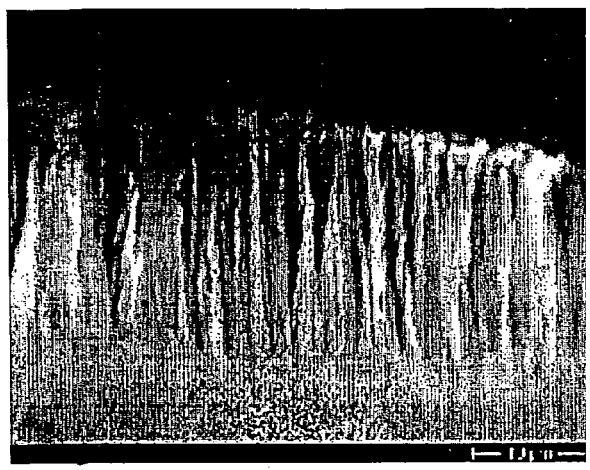
FIG 18:    An SEM image of a section through a glass ceramic that has been obtained by bulk crystallization by annealing at T = 660°C for 4 hours.
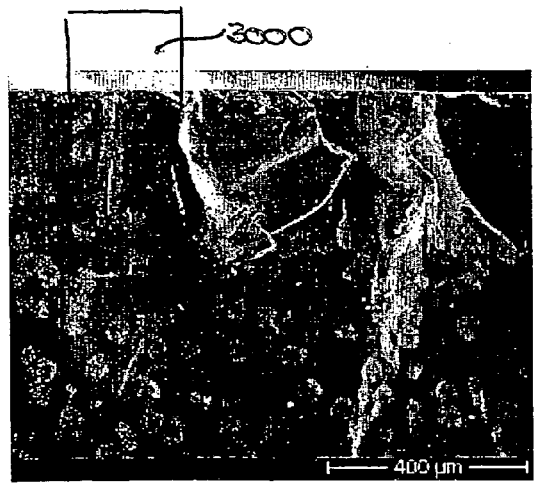

FIG 19: Surface of a glass ceramic ribbon ceramized at a temperature of 700°C, and subsequently treated with water for 15 minutes
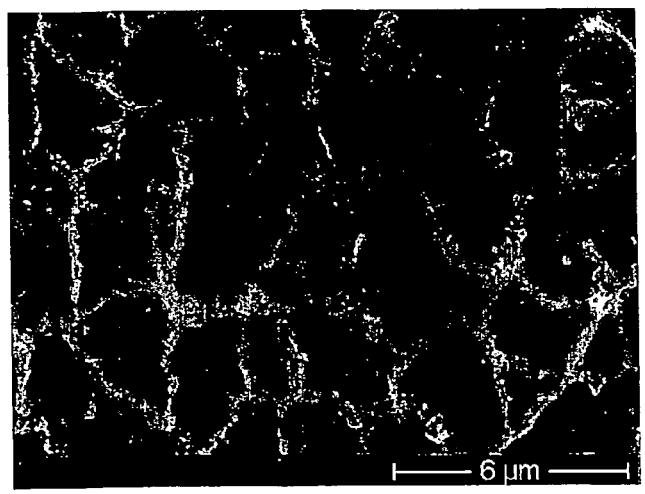

FIGS 20A and B: [Glass ceramic] ceramized at a temperature of 700° C, treated in water for 24 hours
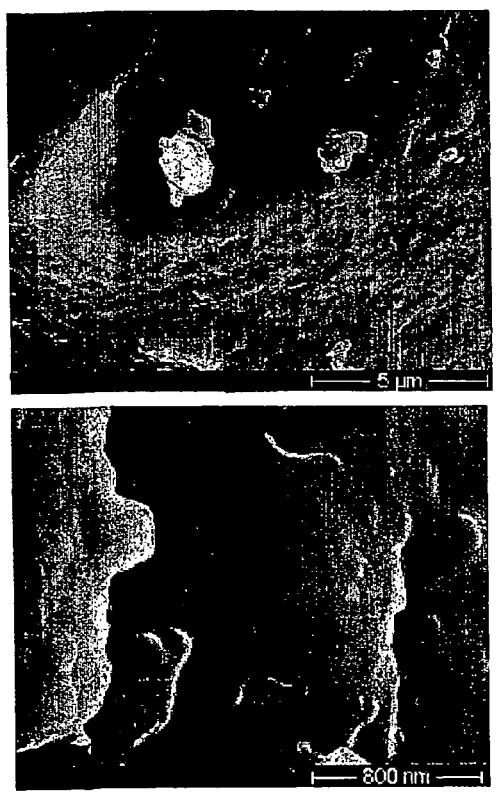

FIGS 21 A and B: [Glass ceramic] ceramized at a temperature of 900° C, treated in water for 24 hours
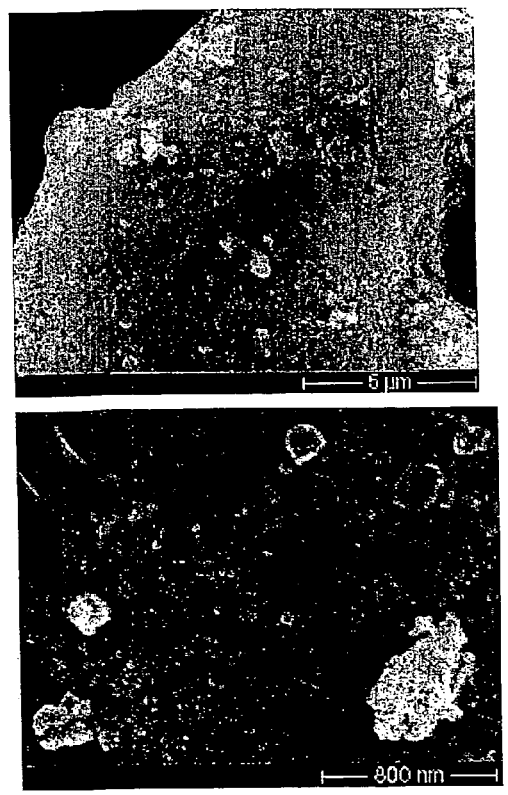

ANTIMICROBIAL ALKALI-SILICATE GLASS CERAMIC AND THE USE THEREOF

The subject of this invention is a glass ceramic with an antimicrobial effect and/or a glass ceramic powder with an antimicrobial effect. The initial glass for the glass ceramic and/or the glass ceramic powder comprises 30–65 percent (by weight) $SiO_2$; 5–30 percent (by weight) $Na_2O$; 5–30 percent (by weight) CaO, and 0–15 percent (by weight) $P_2O_5$.

L L. Hensch, J. Wilson: An Introduction to Bioceramics, World Scientific Publ., 1993, describes glass that has a bioactive and partially antimicrobial effect as a bioglass. Such bioglass is characterized by the formation of hydroxyl apatite layers in aqueous media. Heavy metal-free alkali—alkaline earth—silicate glasses with antimicrobial properties are described in the DE-A-199 32 238 and DE-A-199 32 239 patent applications.

U.S. Pat. No. 5,676,720 discloses a glass powder that comprises 40–60 percent (by weight) $SiO_2$, 5–30 percent (by weight) $Na_2O$, 10–35 percent (by weight) CaO, and 0–12 percent (by weight) $P_2O_5$; furthermore, this patent also discloses glass ceramic that are made of a glass of this composition. However, U.S. Pat. No. 5,676,720 does not provide any information regarding the crystalline phase.

U.S. Pat. No. 5,981,412 describes a bioactive bioceramic material for medical applications with the crystalline phase $Na_2O$—$2CaO$—$3SiO_2$. The crystallite size is around 13 µm. The ceramization is performed by annealing for nucleation and crystallization. The main focus is on mechanical properties such as $K_{1c}$. The crystalline phase portion is between 34 and 60 percent (by volume). U.S. Pat. No. 5,981,412 describes only a crystalline phase that is a high-temperature phase and that forms only under the special conditions indicated in this patent.

The technical task of the present invention is to provide a glass ceramic and/or powder made of such a glass ceramic that—as well as antimicrobial properties—also exhibits inflammation-inhibiting, skin-regenerating, and light-scattering properties.

The invention resolves this task by providing a glass ceramic in accordance with claim 1, wherein the main crystalline phase consists of alkali—alkaline earth—silicates and/or alkaline earth—silicates and/or alkali—silicates.

The glass ceramic and/or the glass ceramic powder as designed by this invention are characterized in that in the visible wavelength range they manifest a defined scattering and reflection effect. In cosmetic application, this effect can diminish the visual appearance of skin wrinkles. Furthermore, towards bacteria, fungi and viruses the glass ceramic demonstrates a biocidal and, definitely, a biostatic effect. However, in contact with humans, the glass ceramic is compatible with skin and is toxicologically harmless.

When used in the cosmetic field, the glass ceramic as designed by this invention has a maximum concentration of heavy metals of, for example, for Pb<20 ppm, Cd<5 ppm, As<5 ppm, Sb<10 ppm, Hg<1 ppm, Ni<10 ppm.

The initial unceramized glass that is used to produce the glass ceramic as designed by the invention contains between 30 and 65 percent (by weight) of $SiO_2$ as the network-forming ion. With a lower concentration, the propensity for spontaneous crystallization strongly increases, and the chemical resistance strongly decreases. With higher $SiO_2$ values, the crystallization stability level can decrease, and the processing temperature can grow significantly, so that the hot-forming properties deteriorate. In addition, $SiO_2$ is also a part of the crystalline phase that arises during the ceramization and must be contained in the glass in an accordingly high concentration if a high crystalline portion is to be created by the ceramization process.

$Na_2O$ is used as the fluxing agent during the melting of glass. With a concentration of less than 5%, the melting process is negatively affected. Sodium is a part of the phases that form during the ceramization process, and thus must be contained in the glass in accordingly high concentrations if a high crystalline portion is to be created by the ceramization process.

$K_2O$ acts as a fluxing agent during the melting of glass. Also, potassium is released in aqueous systems. If potassium is contained in the glass in a high concentration, potassium-containing phases such as potassium silicates are also released. The $K_2O$ content can lie in the range of 0–40 percent (by weight), and preferably in the range of 0–25 percent (by weight), and especially preferred is the range of 0–10 percent (by weight).

The chemical resistance of the glass, and thus the ion release in aqueous media, is controlled by the $P_2O_5$ content. The $P_2O_5$ content is between 0 and 15 percent (by weight). With higher concentrations of $P_2O_5$, the hydrolytic resistance of the glass ceramic diminishes to an insufficient level.

In order to improve its meltability, the glass can contain up to 5 percent (by weight) of $B_2O_3$.

In order not to reach too great a degree of chemical resistance, the quantity of $Al_2O_3$ should be less than 3 percent (by weight). $Al_2O_3$ is used to control the chemical resistance of the glass.

In order to enhance the antimicrobial, and especially the antibacterial properties of the glass ceramic, ions with antimicrobial effects such as Ag, Au, 1, Ce, Cu, Zn, Sn, can be incorporated in concentrations lower than 5 percent (by weight) or lower than 2 percent (by weight). Especially preferred is the addition of Ag. This allows for the formation (in the glass) of especially preferred crystalline phases, such as silver phosphates, e.g., $AgPO_3$ or silicon phosphates $SiP_2O_7$.

Furthermore, ions such as Ag, Cu, Au, and Li, can be incorporated as ingredients in order to control the high temperature conductivity of the molten charge, and thus to improve its meltability by means of a high-frequency melting process.

The concentration of these ions should be lower than 5 percent (by weight).

Coloring ions such as Fe, Cr, Co, and V can be incorporated, individually or in a combined fashion, in a total concentration of less than 1 percent (by weight).

The glass ceramic as designed by the invention is usually used in powder form. The ceramization can be done in the form of a glass block, a glass ribbon, or a glass powder. After ceramization, the glass ceramic blocks or ribbons must be ground to powder. If the powder has been ceramized, it must usually be ground again in order to eliminate agglomerates that have arisen during the ceramization process.

The decisive advantage of the ceramization in the powder form is a very small crystallite size that retains high overall phase portions. In addition, the crystallites grow from the surface of the surface defects that are produced by grinding.

The grinding process generates a large number of surface nuclei, so that many crystals start to grow at the same time, which allows one to obtain a very small crystallite size and, at the same time, a high crystalline phase portion. Therefore, no additional annealing treatment, as has been described in the U.S. Pat. No. 5,981,412 patent, is required to generate nuclei.

The grinding process can occur in dry, aqueous, or non-aqueous media.

Normally, the particle size is less than 500 μm. A useful particle size is <100 μm or <20 μm. Particle sizes that are <10 μm and smaller than 5 μm and smaller than 2 μm are especially useful. The particle size <1 μm has turned out to be exceptionally suitable.

In order to achieve certain effects, mixtures of various glass powders of different compositions from the indicated composition range and with different grain size are possible.

If a block or a ribbon of the initial glass is ceramized, and if crystalline portions of more than 30 percent (by weight) are endeavored, the crystallite sizes are larger than 10 μm. The crystallization occurs very quickly. The ceramization temperatures are between 50° C. and 400° C. above the glass transition temperature, and are preferably between 50° C. and 200° C. above the glass transition temperature, and are also preferably within a range of 50° C. and 100° C. Ceramization can be also performed in a multiple-stage thermal process. The crystallization process is primarily controlled from the surface. Needle-shaped crystals grow from the surface into the glass inside. A few crystals begin to grow in the glass inside. They are spheroidal. Needle-shaped crystals arise during the ceramization of a powder because of the large surface that is used for this process.

The ceramization of the initial glass is controlled from the surface. If, before the ceramization, the ribbons or blocks of the initial glass are ground into powder, the crystallization temperatures decrease significantly. The crystals begin to grow from the surfaces of the powder particles into their insides. The ceramization process can be controlled in such a manner that the particles have only an outer crystalline layer, whereas their insides remain amorphous. The selection of the particle size determines the mean crystal size.

The crystal phase portions in the glass after the ceramization are greater than 5 percent (by weight). Depending on the composition of the initial glass, up to almost 100 percent (by weight) of crystalline phase portions are achieved.

The preferred range is a phase portion between 10 and 30 percent (by weight). Even Still more preferable is the range above 50 percent (by weight).

The crystallite size of the glass ceramic is <10 μm, the preferred size is <5 μm, the especially preferred size is <0.5 μm, and quite especially preferred is <0.1 μn.

Depending on the ceramization temperature, the ceramized powders are re-ground in order to again dissolve any agglomerations that have arisen during the ceramization process.

The main crystal phases are alkali—alkaline earth—silicates and/or alkaline earth silicates, especially NaCa silicates and Ca silicates, and these phase portions can be influenced by ceramization.

Other subsidiary crystal phases that can contain silver and/or phosphorus and/or silicon, such as $AgPO_3$, $SiP_2O_7$, $SiO_2$, can also occur, depending on the particular composition of the initial glass.

Phosphorus-containing glass ceramics from this range of composition can be bioactive in aqueous media; i.e., in aqueous systems they can form a hydroxyl apatite layer on their surface and also on foreign surfaces. Such powders are especially suitable as biomaterials, or they can be used in applications in which remineralization processes play an important role, such as in the fields of hair cosmetics, nail cosmetics, and tooth care.

Using the phases and phase portions, the chemical reactivity and/or the ion release can be influenced. Thus, chemical reactivity and ion releases can be controlled so that the main compatibility, the desired pH value and antimicrobial level, as well as the inflammation-inhibiting effect, can be tailored.

The crystalline phases demonstrate a significantly different chemical resistance than the glass phase. The chemical resistance can be both increased and decreased. Aside from chemical properties, depending on the main crystal phase properties, mechanical, abrasive, and optical properties can also be modified.

In the case of glass ribbons, at a relatively low ceramization temperature <700° C., first one to two Na—Na silicates are formed. These are preferably ($Na_2CaSi_3O_8$/$Na_2CaSiO_4$/$Na_2Ca_2(SiO_3)_3$. Recrystallization occurs at temperatures higher than 700° C.

The resultant crystalline phases partially demonstrate a substantially higher water solubility than the glass phase. Thus, a special adjustment of the phase portions allows one to influence the ion release of the powder, as well as the pH value in an aqueous solution, and thus the biological effect.

The light-scattering effects that cause optical effects such as transparency, reflection, and light scattering, are induced by the different refractive indices of the glass phase and the crystal phase, as well as by the existing crystallite size.

During the dissolution of the crystalline phase in water or an aqueous solution, there remain honeycombed and/or porous surface structures that particularly influence the optical properties, such as transmission, reflection, and light scattering, of the powders in formulations. When solubilized in aqueous systems, the formation of nano particles is observed.

The glass ceramic powders are excellently suited for application in cosmetic products. Among others, these can be products in the field of color cosmetics. Also, the antimicrobial effect allows for application in the field of deodorants and antiperspirants. Moreover, hair and skin care provide other applications within the cosmetic field.

Due to its antimicrobial and inflammation-inhibiting properties, the powder is also suitable for use as an implant material in the medical field and particularly in the field of wound tending.

Furthermore, the material is suitable for use as a carrier substance in the production of artificial three-dimensional tissue structures.

In addition, the powder can be added to polymers, for example, as an antimicrobial active substance. Furthermore, such glass ceramic powders can be used in the fields of paints and lacquers, foodstuff, cleaning agents, paper hygiene, medical products, bioproducts, cosmetic products, and oral care.

The invention is described below using design examples and their attached figures.

FIG. 7 shows a high-temperature X-ray diagram of glass powders with a particle size of approximately 4 µm, depending on the temperature for glass ceramics with an initial glass according to design example 7.

FIG. 8 shows an X-ray diffraction diagram of a crystallized initial glass with a composition according to design example 8, annealed for 4 hours at 650° C.

FIG. 9 shows an X-ray diffraction diagram of a crystallized initial glass with a composition according to design example 8, annealed for 4 hours at 700° C.

FIG. 10 shows an X-ray diffraction diagram of a crystallized initial glass with a composition according to design example 8, annealed for 4 hours at 900° C.

FIG. 11 shows an X-ray diffraction diagram of a crystallized initial glass with a composition according to design example 9, annealed for 4 hours at 560° C.

FIG. 12 shows an X-ray diffraction diagram of a crystallized initial glass with a composition according to design example 9, annealed for 4 hours at 700° C.

FIG. 13 shows an X-ray diffraction diagram of a crystallized initial glass with a composition according to design example 9, annealed for 4 hours at 900° C.

FIG. 14 shows a DTA analysis of a initial glass ceramized as a glass block according to design examples 8 and 9.

FIG. 15 shows the standardized bacidity for a glass ceramic ceramized at various temperatures based on an initial glass with a composition according to design example 1

FIG. 16 shows the standardized conductivity for a glass ceramic ceramized at various temperatures based on an initial glass with a composition according to design example 1

FIG. 17 shows a SEM image of surface crystals on the surface of a glass ceramic that has been obtained by annealing an initial glass according to design example 1 at 660° C. for 4 hours.

FIG. 18 shows a SEM image of a section through a glass ceramic that has been obtained by means of bulk crystallization by annealing at T=660° C. for 4 hours.

FIG. 19 shows the surface of a glass ceramic ribbon ceramized at 700° C., and subsequently treated with water for 15 minutes.

FIGS. 20A–B show the surface of a glass ceramic ribbon ceramized at 700° C., and subsequently treated in water for 24 hours.

FIGS. 21A–B show the surface of a glass ceramic ribbon ceramized at 900° C., and subsequently treated in water for 24 hours.

A glass was produced by melting raw materials. The melting occurred in platinum crucibles at a temperature of 1550° C. Subsequently, the molten material was formed into ribbons. These ribbons were then further processed by dry grinding into a powder with a particle size of d50=4 µm.

Table 1 indicates the composition of the initial glasses in percent (by weight) for all glass ceramics described in the following text.

TABLE 1

Composition (synthesis value) [In percent (by weight)]

| Example | 1 | 2 | 3 | 4 | 5 | 6 | 7 | 8 | 9 | 10 | 11 |
|---|---|---|---|---|---|---|---|---|---|---|---|
| $SiO_2$ | 46.0 | 35 | 46 | 50 | 40 | 59 | 45 | 44.9 | 35 | 45 | 65 |
| $Al_2O_3$ | 0 | 0 | 0 | 0 | 0 | 0 | 1 | 0 | 0 | 0 | 0 |
| CaO | 25.0 | 29 | 20 | 10 | 25 | 20 | 25 | 24.5 | 29.0 | 23.5 | 10.0 |
| MgO | 0 | 0 | 0 | 0 | 0 | 0 | 0 | 0 | 0 | 0 | 0 |
| $Na_2O$ | 25.0 | 30 | 20 | 25 | 25 | 20 | 24 | 24.5 | 29.5 | 24.5 | 20.0 |
| $K_2O$ | 0 | 0 | 0 | 0 | 0 | 0 | 0 | 0 | 0 | 0 | 0 |
| $P_2O_5$ | 4.0 | 6 | 0 | 15 | 0 | 1 | 7 | 0 | 0 | 0 | 5.0 |
| $Ag_2O$ | 0 | 0 | 0 | 0 | 0 | 0 | 0 | 0.1 | 0.1 | 0 | 0 |
| ZnO | 0 | 0 | 0 | 0 | 0 | 0 | 0 | 0 | 0 | 1.0 | 0 |

If we use the initial glasses indicated in Table for the production of glass ceramics, we discover that the glasses according the design examples 2 and 9 already demonstrate a strong propensity for crystallization during the melting process. Therefore, in the case of these initial glasses, it is necessary to cool them off especially quickly. If a partial or a complete ceramization already occurs during the melting of the glass, the glass ceramic can be subjected to a new annealing at the indicated temperatures in order to obtain the crystal phases described in this patent application.

Figure 1:
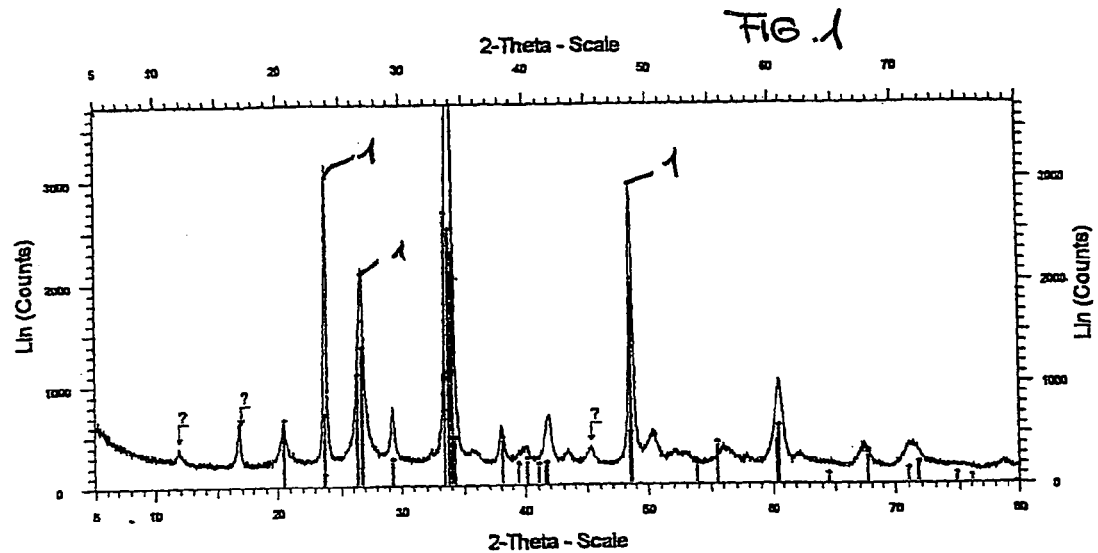
FIG. 1 shows an X-ray diffraction diagram of an initial glass crystallized in powder form with a composition according to the design example 1, annealed for 5 hours at 650° C.
Figure 2:
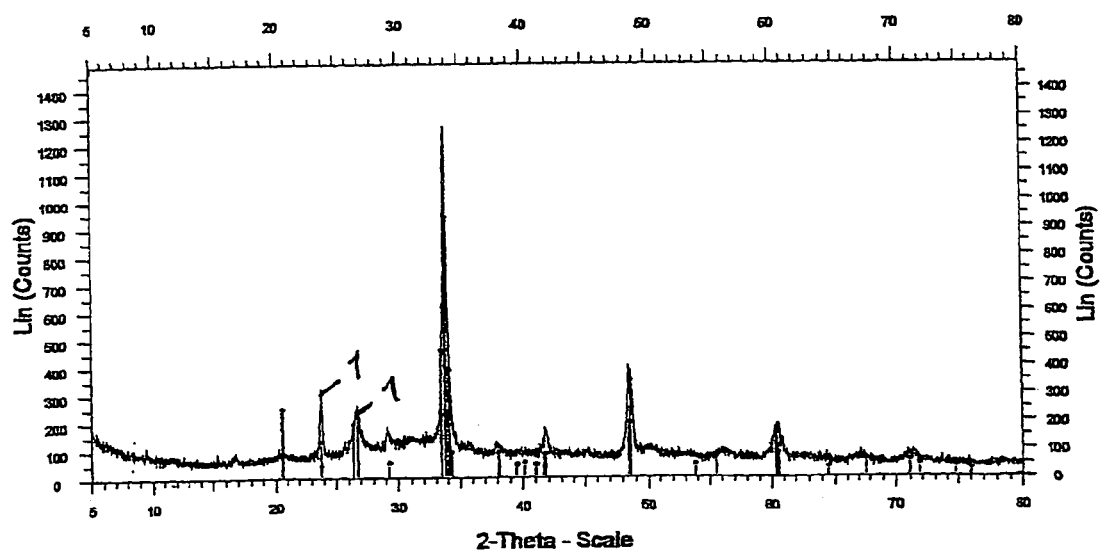
FIG. 2 shows an X-ray diffraction diagram of an initial glass crystallized in powder form, annealed for 5 hours at 590° C.
Figure 3:
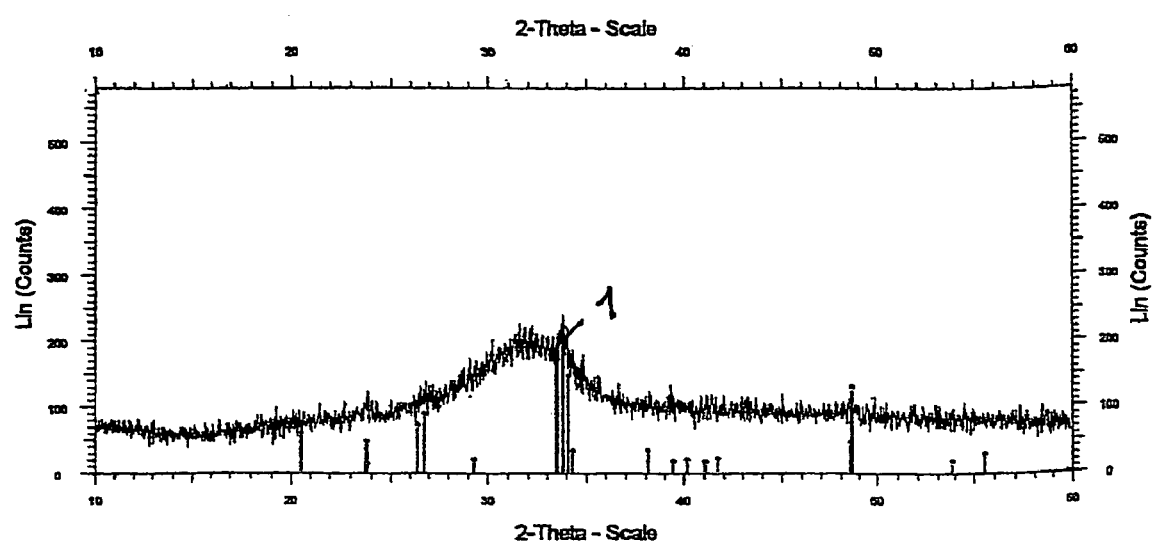
FIG. 3 shows an X-ray diffraction diagram of an initial glass crystallized in powder form, annealed for 5 hours at 560° C.

FIGS. 1–3 show X-ray diffraction diagrams of initial glasses crystallized in powder form according to the design example 1 in Table 1, annealed for 5 hours at 650° C. (FIG. 1), 590° C. (FIG. 2), and 560° C. (FIG. 3). Clearly recognizable is the decrease in intensity of the diffraction orders 1 related to the crystal phases, which is synonymous with a decreasing crystal proportion in the glass ceramic.

For example, the intensity peaks can be ascribed to the $Na_2CaSiO_4/Na_2OCaSiO_2$ and $Na_2CaSi_3O_8$ crystal phases.

Figure 4:
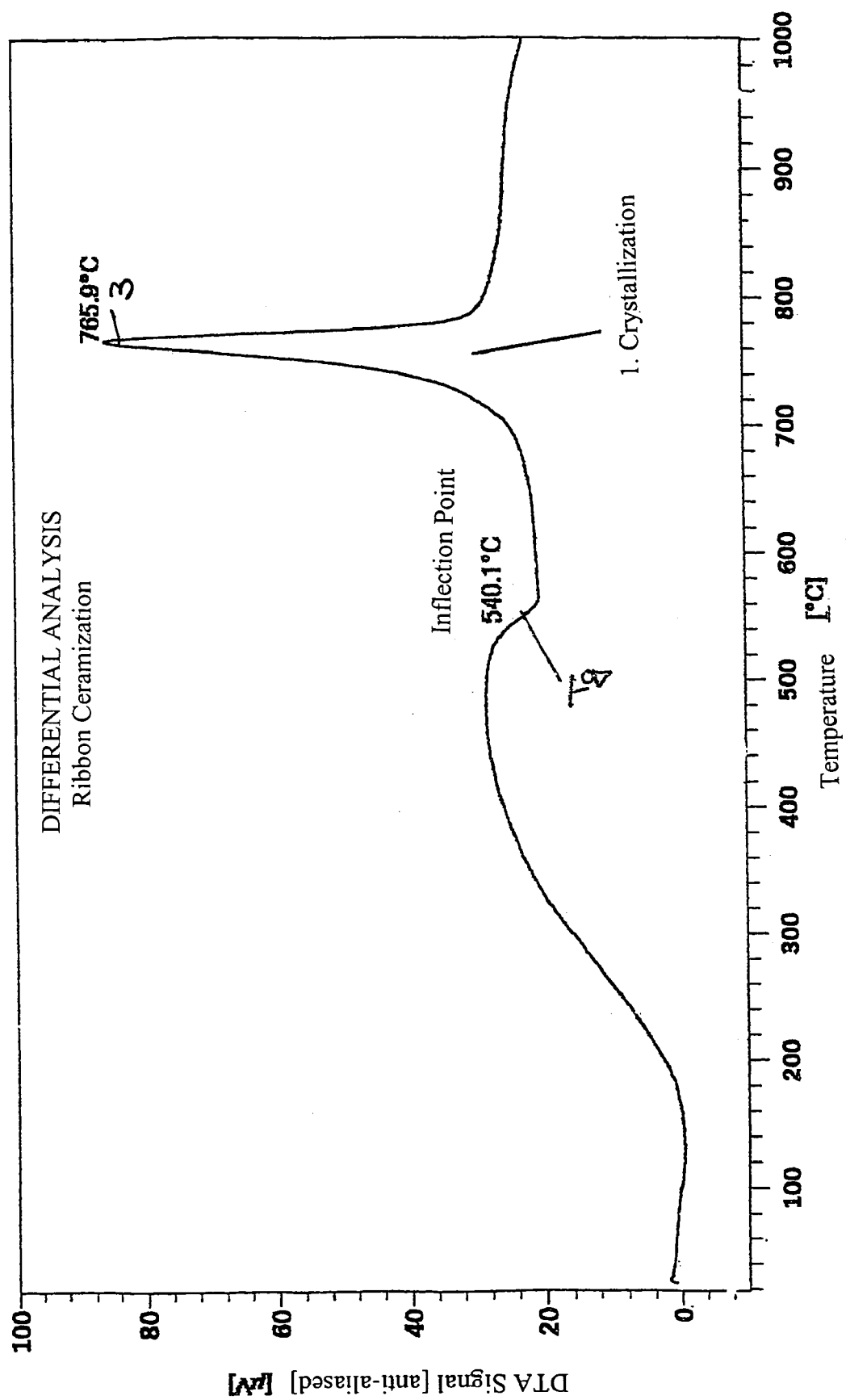
FIG. 4 shows a DTA analysis of an initial glass ceramized as a glass block according to design example 1.
Figure 5:
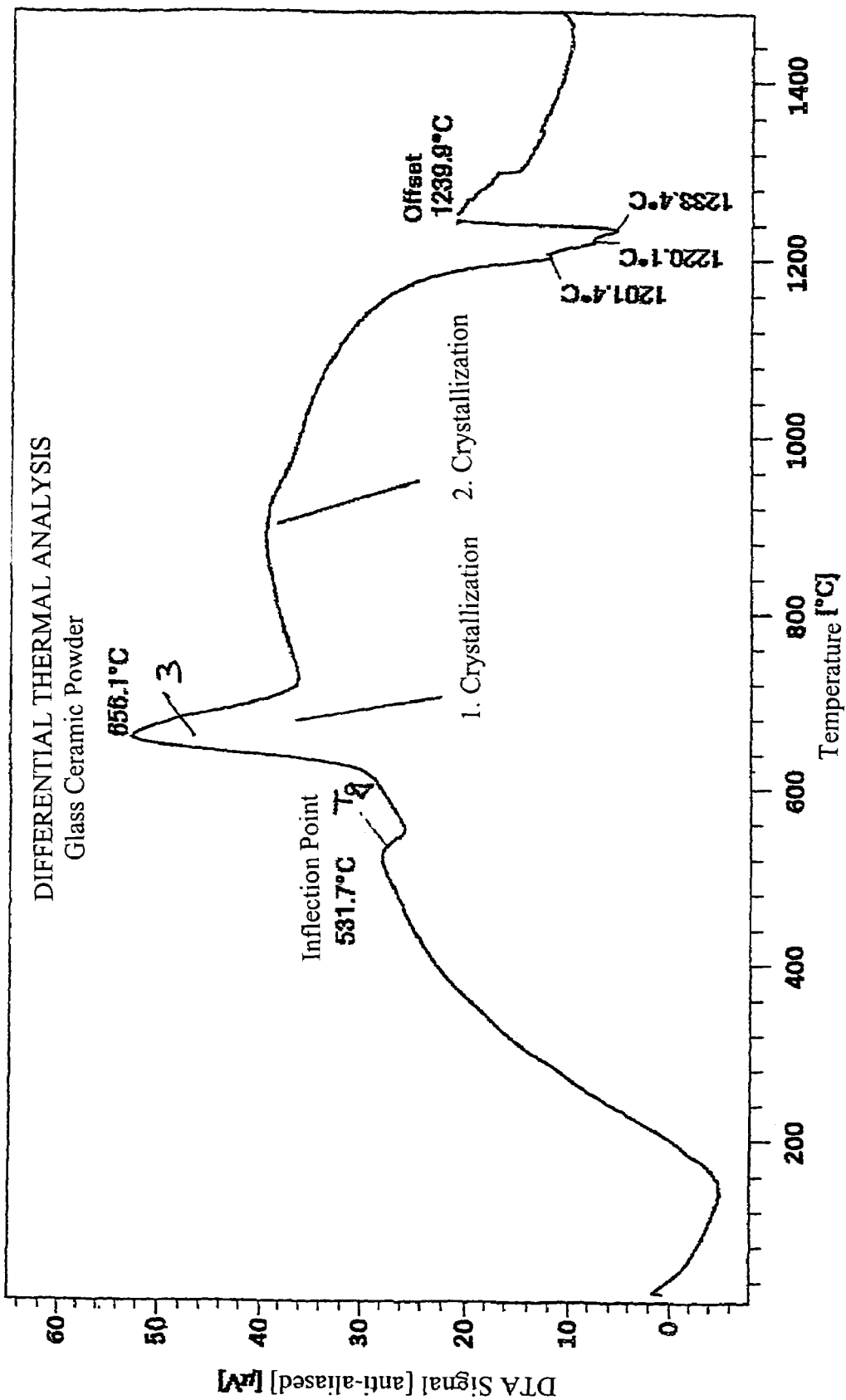
FIG. 5 shows a DTA analysis of an initial glass ceramized in powder form according to design example 1.
Figure 6:
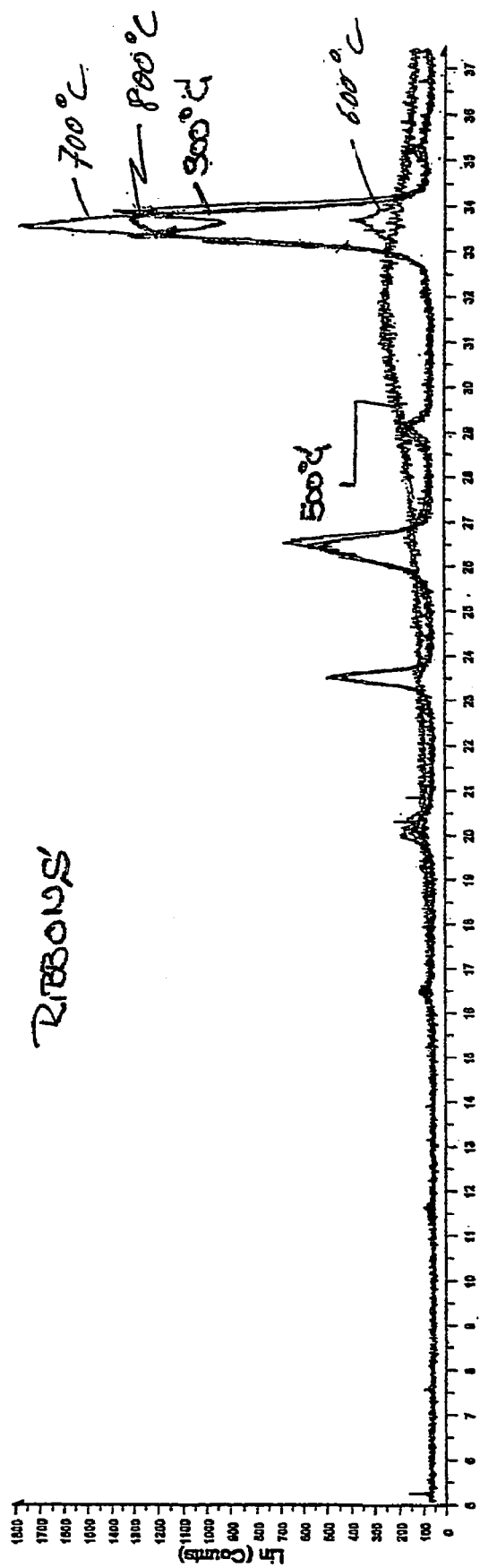
FIG. 6 shows an X-ray diffraction diagram of glass ribbons ceramized at various temperatures according to design example 1.

At higher temperatures, a recrystallization occurs, as is apparent from FIG. 6. At temperatures >900° C., Ca silicates can form, too. FIGS. 4 and 5 show the DTA analysis of an initial glass ceramized as a glass ribbon according to the design example 1 in Table 1 (FIG. 4), and an initial glass ceramized in powder form (FIG. 5) with a heating rate of 10 K/min. Clearly recognizable is the crystallization peak 3 for the crystal phase, whose temperatures are lower for the initial glass ceramized in powder.

FIG. 5 also shows the slightly exothermal reaction of the re-crystallization.

FIG. 7 shows high-temperature X-ray diagrams for a glass ceramic powder that has been obtained from an initial glass according to the design example 7, depending on the temperature. Re-crystallization occurs at higher temperatures (over 900° C.). The X-ray measurements were recorded during the heating process. At these temperatures, Ca silicates can also form. FIG. 7 shows 2000.1 and 2000.2, which according to the JCPDS database, designate the $Na_2CaSiO_4$ phase, and 2002.1 and 2002.2, which according to the JCPDS database designate the $Na_2CaSi_3O_8$ phase. As is apparent from FIG. 7, the $Na_2CaSi_3O_8$ phase forms only at a temperature above 900° C. The properties of various glass ceramics, produced in various different ways based on the initial glass according to the example 1 in Table 1, are indicated in Table 2.

TABLE 2

Properties of glass ceramics according to the design example 1

| | Annealing time | Crystallite size | Main crystalline phases | JCPDS Database |
|---|---|---|---|---|
| Powder 580° C. | 5 hours | <0.5 | $Na_2CaSi_3O_8$/ $Na_2CaSiO_4$ $Na_2Ca_2(SiO_3)_3$ | 12-0671/24- 10696 |
| Powder 650° C. | 5 hours | <1 | $Na_2CaSi_3O_8$/ $Na_2CaSiO_4$ $Na_2Ca_2(SiO_3)_3$ | 12-0671/24- 10696 |
| Powder 700° C. | 5 hours | <15 | $Na_2CaSi_3O_8$/ $Na_2CaSiO_4$ $Na_2Ca_2(SiO_3)_3$ | 12-0671/24- 10696 |
| Ribbons 700° C. | 5 hours | >100 μm | $Na_2CaSi_3O_8$/ $Na_2CaSiO_4$ $Na_2Ca_2(SiO_3)_3$ | 12-0671/24- 10696 |
| Ribbons 600° C. | 2 hours | >20 μm in volume | $Na_2CaSi_3O_8$/ $Na_2CaSiO_4$ $Na_2Ca_2(SiO_3)_3$ | 12-0671/24- 10696 |

Table 3 shows the antibacterial effect of a glass ceramic powder that was annealed at 580° C. for 5 hours with a grain size of 4 μm.

TABLE 3

Antibacterial effect of the powder according to Europ. Pharmakopoe (3. edition): Design example 1 (grain size 4 μm)

| | E. coli | P. aeruginosa | S. aureus | C. albicans | A. niger |
|---|---|---|---|---|---|
| Start | 290,000 | 270,000 | 250,000 | 300,000 | 250,000 |
| 2 days | 900 | 1,800 | 800 | <100 | 2,000 |
| 7 days | <100 | 200 | <100 | 0 | 2000 |
| 14 days | 0 | 0 | 0 | 0 | 0 |
| 21 days | 0 | 0 | 0 | 0 | 0 |
| 28 days | 0 | 0 | 0 | 0 | 0 |

No irritation has been determined by skin compatibility tests, i.e., oculsive tests over 24 hours.

Table 4 indicates in detail, and in a tabular form, exemplary main crystalline phases of Na—Ca silicate systems using the basic formula

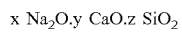

x $Na_2O$.y CaO.z $SiO_2$ and the numbers for x, y, and z.

TABLE 4

Main Crystalline phase in Na—Ca silicate systems

| $Na_2O$ (x) | CaO (y) | $SiO_2$ (z) |
|---|---|---|
| 1 | 3 | 6 |
| 1 | 1 | 5 |
| 1 | 2 | 3 |
| 1 | — | 2 |
| 3 | — | 8 |
| 2 | 3 | 6 |
| 2 | — | 2 |
| 0 | 1 | 1 |
| 1 | 0 | 1 |

The results of the glass ceramics that have been obtained from the initial glasses according to design examples 8 and 9 are described in the following text.

FIGS. 8–10 show the X-ray diffraction diagrams of initial glasses crystallized in powder form according to the design example 8 in Table 1, and annealed for 4 hours at 560° C. (FIG. 8), 700° C. (FIG. 9), and 900° C. (FIG. 10). The phase determined from the intensity peaks is a Na—Ca silicate, namely $Na_6Ca_3Si_6O_{18}$ (JCPDS 77-2189) as a crystalline phase. Clearly recognizable is the change of the Na—Ca ratio in tandem with the increase in temperature.

FIGS. 11–13 show the X-ray diffraction diagrams of initial glasses crystallized in powder form according to the design example 9 in Table 1, and annealed for 4 hours at 560° C. (FIG. 11), 700° C. (FIG. 12), and 900° C. (FIG. 13). Two Na—Ca silicates $Na_2CaSiO_4$ (JCPDS 73-1726) and $Na_2Ca_2SiO_7$ (JCPDS 10-0016), as well as the silicon phosphate $SiP_2O_7$ (JCPDS 39-0189) and cristobalite $SiO_2$ (JCPDS 82-0512) can be identified in FIGS. 11–13 as the main crystalline phases. The samples produced at 700° C. and 900° C. that are shown in Tables 12 and 13 contain another crystalline phase, namely the silver phosphate $AgPO_3$ (JCPDS 11-0641). The portion of this phase is higher in the sample produced at 900° C. than in the sample produced at 700° C.

FIG. 14 shows the DTA thermo-analysis of an initial glass ceramized as a glass ribbon according to design examples 8 and 9 in Table 1 with heating rates of 10 K/min. The crystallization peak 3 for the crystal phase is clearly recognizable from design example 8 . The glass ceramic that is based on the initial glass according to design example 9 is a glass ceramic that has already been crystallized from the molten charge. No strong exothermal signal is observed in the DTA, because the subsequent crystallization or re-crystallization only releases a little heat. The reason for this phenomenon is that the initial glass in this design example has a propensity for spontaneous crystallization to occur during the melting process.

Table 5 shows the antibacterial properties of a glass ceramic powder that, based on an initial glass according to design example 8, was annealed at 560° C. with a grain size of 4 μm.

TABLE 5

Antibacterial effect of powders according to Europ. Pharmakopoe (3. edition): Design example 8 annealed at 560° C. (grain size 4 μm)

| | E. coli | P. aeruginosa | S. aureus | C. albicans | A. niger |
|---|---|---|---|---|---|
| Start | 290,000 | 270,000 | 250,000 | 300,000 | 250,000 |
| 2 days | 700 | 2,000 | 500 | <100 | 2,000 |
| 7 days | 0 | 0 | 0 | 0 | 0 |
| 14 days | 0 | 0 | 0 | 0 | 0 |
| 21 days | 0 | 0 | 0 | 0 | 0 |
| 28 days | 0 | 0 | 0 | 0 | 0 |

Table 6 shows the antibacterial properties of a glass ceramic powder that, based on an initial glass according to design example 9, was annealed at 900° C. with a grain size of 4 μm.

TABLE 6

Antibacterial effect of powders according to Europ. Pharmakopoe (3. edition): Design example 9 (grain size 4 μm)

| | E. coli | P. aeruginosa | S. aureus | C. albicans | A. niger |
|---|---|---|---|---|---|
| Start | 290,000 | 270,000 | 250,000 | 300,000 | 250,000 |
| 2 days | 0 | 0 | 0 | 0 | 0 |
| 7 days | 0 | 0 | 0 | 0 | 0 |
| 14 days | 0 | 0 | 0 | 0 | 0 |

TABLE 6-continued

Antibacterial effect of powders according to Europ. Pharmakopoe
(3. edition): Design example 9 (grain size 4 μm)

| | E. coli | P. aeruginosa | S. aureus | C. albicans | A. niger |
|---|---|---|---|---|---|
| 21 days | 0 | 0 | 0 | 0 | 0 |
| 28 days | 0 | 0 | 0 | 0 | 0 |

Table 7 indicates, in detail, and in a tabular form, the main crystalline phases found in the produced samples using the basic formula x $Na_2O \cdot y\ CaO \cdot z\ SiO_2$ and the numbers for x, y, and z.

Besides the Na—Ca phases, a silicon phosphate phase is also found. In addition, a silver phosphate phase is found at high temperatures above 700° C.

TABLE 7

Main crystalline phases of the glass ceramics,
design examples 8 and 9

| $Na_2O$ (x) | CaO (y) | $SiO_2$ (z) | $Ag_2O$ | $P_2O_5$ | Note |
|---|---|---|---|---|---|
| | | | 1 | 1 | From 700° C. |
| 3 | 3 | 6 | | | |
| 1 | 1 | 1 | | | |
| 1 | 2 | 1 | | | |
| | | | 1 | 1 | |
| 2 | 1 | 3 | | | |

Table 8 indicates the pH values and the conductivity of a 1% suspension of a glass ceramic powder that comprises an initial glass according to design example 7 in Table 1, for various annealing conditions for the production of glass ceramic. The annealing conditions include annealing time and annealing temperature. Depending on the annealing time and the annealing temperature, different main crystal phases develop in the glass ceramic.

TABLE 8 pH value and conductivity of a glass ceramic powder that has crystallized
from an initial glass according to design example 7

| Annealing conditions | After 15 minutes Ph value | Conductivity (μS/cm) | After 50 minutes Ph value | Conductivity (μS/cm) | After 24 hours Ph value | Conductivity (μS/cm) |
|---|---|---|---|---|---|---|
| Untreated | 11.3 | 695 | 11.3 | 900 | 11.7 | 1,872 |
| 500° C. - 2 hours | 11.1 | 526 | 11.2 | 623 | 11.4 | 1,054 |
| 600° C. - 2 hours | 11.2 | 571 | 11.2 | 686 | 11.5 | 1,130 |
| 700° C. - 2 hours | 11.2 | 576 | 11.2 | 679 | 11.5 | 1,007 |
| 800° C. - 2 hours | 11.2 | 619 | 11.3 | 749 | 11.5 | 1,238 |
| 900° C. - 2 hours | 11.3 | 859 | 11.4 | 949 | 11.6 | 1,288 |

FIGS. 15 and 16 show the pH value, i.e., the standardized bacidity and the standardized conductivity for a glass ceramic obtained by annealing for 2 hours at various temperatures based on an initial glass according to design example 1.

FIGS. 15 and 16 include the following reference numbers:

100: The unceramized initial glass according to design example 1

102: The initial glass according to design example 1 that has been ceramized at 600° C. for 2 hours 104: The initial glass according to design example 1 that has been ceramized at 700° C. for 2 hours 106: The initial glass according to design example 1 that has been ceramized at 800° C. for 2 hours 108: The initial glass according to design example 1 that has been ceramized at 900° C. for 2 hours By standardized bacidity and standardized conductivity, we understand the bacidity and the conductivity standardized for the surface. These properties are independent of the actual particle size. Conductivity is indicated per surface ($cm^2$) and mass (g) of powder.

Table 9 shows the ion release rate of an unceramized powder and glass ceramic powder in a 1% suspension that comprises, as the initial glass, a glass according to design example 7 in Table 1. The glass ceramic powder has been produced by annealing at a temperature of 650° C. for 4 hours.

TABLE 9

Ion release rate (1% suspension, unit: mg/L)

| | Not ceramized | Powder ceramized at 650° C. |
|---|---|---|
| Na | 96.7 mg/Liter | 63.2 mg/Liter |
| Ca | 29.8 mg/Liter | 21.5 mg/Liter |
| Si | 63.5 mg/Liter | 40.3 mg/Liter |
| P | 0.22 mg/Liter | 0.67 mg/Liter |
| pH | 11.3 | 11.3 |
| Conductivity | 635 μS/cm | 432 μS/cm |

The following text describes the scanning of electron micrograph images (SEM images) of glass ceramics that have been obtained by crystallizing the initial glass according to design example 1.

FIG. 17 shows a SEM image of the surface of a glass ceramic that has been obtained by annealing an initial glass according to design example 1 at a temperature of 660° C. for 4 hours. The surface crystals on the ribbon are clearly recognizable. Parts of these surface crystals can be soluble in water so that, during a treatment with water, these crystals are dissolved, and a honeycomb structures remains. Furthermore, this crystalline surface can release certain phases, such as nano particles that, among other things, are important for applications in oral care, i.e., for the use of glass ceramic as designed by the invention in the field of tooth and oral care. Furthermore, the crystalline surface shown in this figure demonstrates light-scattering properties that can be used for certain applications.

While FIG. 17 shows the surface structure of the glass ceramic, FIG. 18 shows a SEM image of the crystallization inside the glass block, that is, the bulk crystallization. FIG. 17 is a section of FIG. 18. The section is marked in FIG. 18 with 3000. The glass ceramic shown in FIGS. 17 and 18 has been obtained by annealing [the initial glass] at a temperature of 660° C. for 4 hours. The formed crystallites in FIG. 18 are clearly recognizable as round points. The crystals formed in the bulk crystallization have light-scattering properties that can be used for certain applications. In FIGS. 17 and 18, crystallization occurred in the glass block (ribbon). Both FIG. 17 and FIG. 18 show a cross-section of the surface of the block (ribbon). FIG. 17 is a section of FIG. 18, and shows the surface in detail.

FIG. 19 shows the surface of a glass ceramic ribbon that has been obtained by ceramizing an initial glass according to the design example 1 at 700° C. for 4 hours. The glass ceramic was subsequently treated with $H_2O$. The easily soluble crystalline phases essentially comprising Na—Ca silicate are dissolved. There remains a "honeycomb" structure that can be easily recognized in FIG. 19.

FIGS. 20A–B show the surface of a glass ceramic powder that has been obtained by ceramizing an initial glass according to design example 1 at 700° C. for 4 hours. The surface shown has been obtained by treating the glass ceramic powder with water for 24 hours.

Furthermore, we can recognize a certain surface coarseness in FIGS. 20A and 20B. As is apparent from the figures, the surface is relatively homogeneous, and does not show any formation of nano particles.

FIGS. 21A–B show the surface of a glass ceramic powder that has been obtained by ceramizing an initial glass according to design example 1 at a temperature of 900° C. for 4 hours. In contrast to the smooth surface obtained at lower annealing temperatures, as shown in FIGS. 20A and 20B, FIGS. 21A and 21B show the released nano crystals and a porous surface structure.

The crystalline nano particles are less soluble in water. The nano particles were formed during the annealing process, and have been released from the surface.

The released nano particles are important for, among other things, applications in oral care, because they have a desensitizing effect on the tooth nerve. The desensitizing effect is achieved in that the nano particles are able to close the tubulin channels.

The present invention provides a glass ceramic powder and a glass ceramic that can be used in a number of fields; for example, in the fields of cosmetics or food supplements, and in the medical field.

The invention claimed is:

1. Glass ceramic formed from an initial glass comprising:
   30–65 percent (by weight) of $SiO_2$
   5–30 percent (by weight) of $Na_2O$
   5–30 percent (by weight) of CaO
   0–15 percent (by weight) of $P_2O_5$,
   wherein the glass ceramic includes crystalline phases comprising at least one silicate selected from the group consisting of alkali metal silicates and alkaline earth metal silicates having a crystallite size <0.1 µm.

2. Glass ceramic according to claim 1, wherein the initial glass comprises:
   30–<47 percent (by weight) of $SiO_2$
   10–30 percent (by weight) of $Na_2O$
   10–30 percent (by weight) of CaO
   2–15 percent (by weight) of $P_2O_5$.

3. Glass ceramic according to claim 1, wherein the crystalline phases comprise at least one silicate selected from the group consisting of sodium silicates and potassium silicates.

4. Glass ceramic according to claim 1, wherein the crystalline phases are water-soluble phases comprising at least one silicate selected from the group consisting of sodium silicates and calcium silicates.

5. Glass ceramic according to claim 1, wherein the initial glass further comprises 0–40 percent (by weight) of $K_2O$ as well as 0–5 percent (by weight) of $Al_2O_3$.

6. Glass ceramic according to claim 1, wherein the initial glass comprises 0–40 percent (by weight) of MgO and 0–50 percent (by weight) of $B_2O_3$.

7. Glass ceramic according to claim 1, wherein the glass ceramic comprises ions with a total portion of <2 percent (by weight).

8. Glass ceramic according to claim 7, wherein the ions include at least one ion selected from the group consisting of Ag, Au, I, Zn, Cu, and Ce ions.

9. Glass ceramic powder that comprises a glass ceramic according to claim 1, wherein the glass ceramic powder has a particle size of <100 µm.

10. Glass ceramic powder that comprises a glass ceramic according to claim 1, wherein the glass ceramic powder has a particle size of <20 µm.

11. Glass ceramic powder that comprises a glass ceramic according to claim 1, wherein the glass ceramic powder has a particle size of <5 µm.

12. Glass ceramic powder that comprises a glass ceramic according to claim 1, wherein the glass ceramic powder has a particle size of <1 µm.

13. Method for the production of a glass ceramic powder having a particle size of <100 µm, comprising the steps of providing the initial glass of claim 1, grinding the initial glass, and ceramizing the ground initial glass.

* * * * *